United States Patent [19]
Kurono et al.

[11] Patent Number: 4,857,521
[45] Date of Patent: Aug. 15, 1989

[54] TRIALKYLSILYL PYRIDINIUM CEPHALOSPORIN ANTIBIOTICS

[75] Inventors: Masayasu Kurono, Sasao; Yutaka Baba, Iwakura; Takahiko Mitani, Mie; Masao Onishi; Yasuaki Kondo, both of Kasugai; Kiichi Sawai, Funabashi, all of Japan

[73] Assignee: Sanwa Kagaku Kenkyusho Co., Ltd., Nagoya-shi, Japan

[21] Appl. No.: 6,199

[22] Filed: Jan. 23, 1987

[30] Foreign Application Priority Data

Jan. 29, 1986 [JP] Japan .................. 61-15821

[51] Int. Cl.$^4$ .................. C07D 501/38; A61K 31/545
[52] U.S. Cl. ..................... 514/206; 540/225
[58] Field of Search .................. 540/225; 514/206

[56] References Cited

U.S. PATENT DOCUMENTS

| | | | |
|---|---|---|---|
| 3,449,338 | 6/1969 | Flynn | 260/243 |
| 4,152,432 | 5/1979 | Heymes et al. | 424/246 |
| 4,504,777 | 3/1985 | O'Calloghan et al. | 540/225 |
| 4,600,772 | 7/1986 | O'Calloghan et al. | 540/225 |

*Primary Examiner*—Nicholas S. Rizzo
*Attorney, Agent, or Firm*—Armstrong, Nikaido, Marmelstein, Kubovick & Murray

[57] ABSTRACT

A cephalosporin derivative represented by the formula

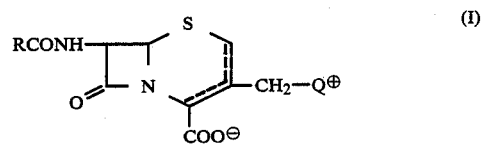

(I)

wherein R is an organic residue known on β-lactam antibiotics and Q is a radical of

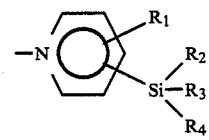

dotted-line means a possible double bond, $R_1$ is hydrogen or mono-valent substituent, $R_2$, $R_3$ and $R_4$ are mono-valent substituent, respectively, a salt thereof, a process for the manufacture thereof and a pharmaceutical agent comprising same.

8 Claims, No Drawings

TRIALKYLSILYL PYRIDINIUM CEPHALOSPORIN ANTIBIOTICS

BACKGROUND OF THE INVENTION

1. Field of the Invention

The present invention relates to a novel cephalosporin derivative, a salt thereof, a process for the manufacture of same and a pharmaceutical agent comprising same.

2. Related Arts

A study on cephalosporins has been started from a separation of several antibiotics from a culture solution for Cephalosporium acremonium, which were given a name to Cephalosporin $P_1$ to $P_5$ and N, respectively. Thereafter, Cephalosporin C has been isolated from a crude Cephalosporin N.

This Cephalosporin C has a wide antibacterial spectrum to prevent the growth of Gram-positive and negative pathogens, but shows a drawback of a relatively low antibacterial power.

Therefore, various derivatives of the Cephalosporin C have been developped, in which acetoxymethyl radical in 3-position is substituted with another radical or D-α-aminoadipic acid radical bonded to amino radical in 7-position is substituted with another acid radical. As examplar compounds among the derivatives, there are Cephaloridine namely 7-(2-thienyl)acetamido-3-pyridin-1-yl-methyl-3-cephem-4-carboxylate (U.S. Pat. No. 3,449,338), Cephotaxim namely sodium 7-[2-(2-aminothiazol-4-yl)-2-methoxyiminoacetamido]-3-acetoxymethyl-3-cephem-4-carboxylate (U.S. Pat. No. 4,152,432) and the like.

Each of the Cephalosporin C derivatives has the antibacterial spectrum wider than that of penicillins, is effective also to infectious diseases due to Gram-negative pathogens, can be dosed to patients with a penicillin hyperergy due to its low cross allergie to penicillins, and show a relatively low crossed tolerance to penicillins. Therfore, some of those inclusive of said Cephaloridine have already hold a remarkable position in crinical view points.

In order to further develop antibiotical therapy by cephalosporin compounds, however, those having more wide antibacterial spectrum and showing more high activity to fast bacterias and more particularly to Gram-negative pathogens have highly been demanded.

SUMMARY OF THE INVENTION

A principal object of the invention is to provide novel cephalosporin derivatives having a wide antibacterial spectrum to make its applicable infectious diseases wider, a high activity to show a high antibacterial power, and a low toxicity to provide a great safety in its use.

Another object of the invention lies in providing a process for the manufacture of such excellent cephalosporin derivatives.

A further object of the invention is to provide an agent for curing infectious diseases, which comprises at least one of the derivatives and salts thereof, as an effective component.

As apparently known, an antibacterial power of each cephalosporin derivative, when the β-lactam ring in its structural skelton be opened or broken, similar to the case in penicillins.

Therefore, the inventors have carefully studied with paying their possible efforts to finally find out novel cephalosporin derivatives with pyridinium methyl radical in its 3-position, which show a relatively high stability to β-lactamase and have a relatively wide antibacterial spectrum.

The cephalosporin derivatives according to the invention are shown by the formula of

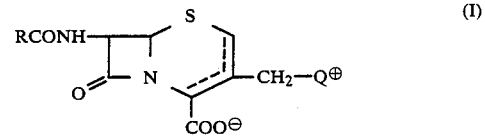

wherein R is an organic residue known on β-lactam antibiotics and Q is a radical of

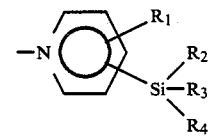

dotted-line means a possible double bond, $R_1$ is hydrogen or mono-valent substituent, $R_2$, $R_3$ and $R_4$ are mono-valent substituent, respectively.

As the organic residue R, followings may be listed as typical ones.

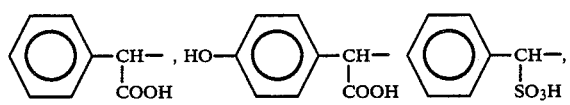

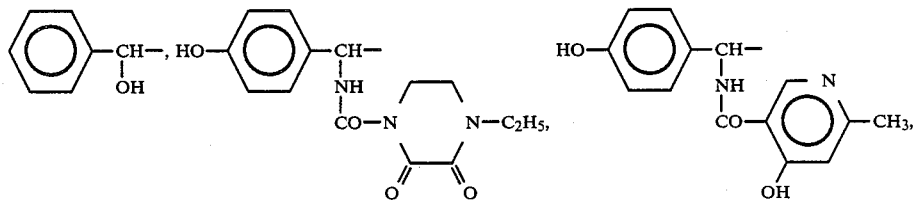

-continued
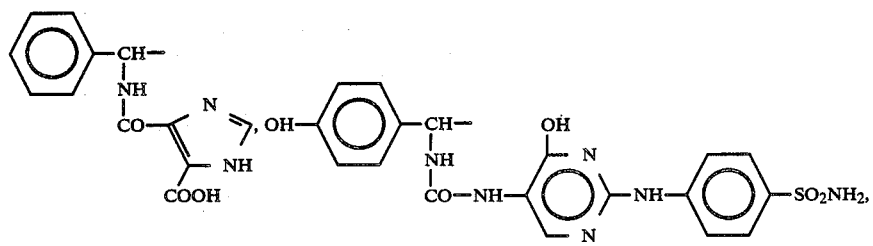
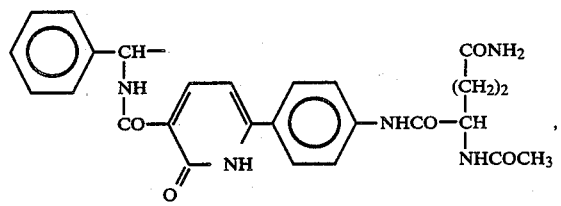
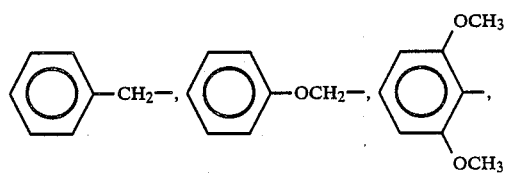
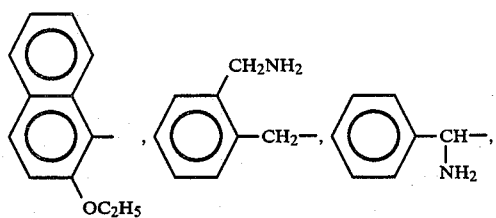
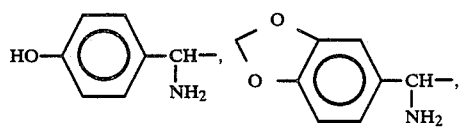
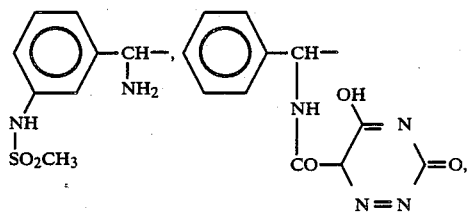
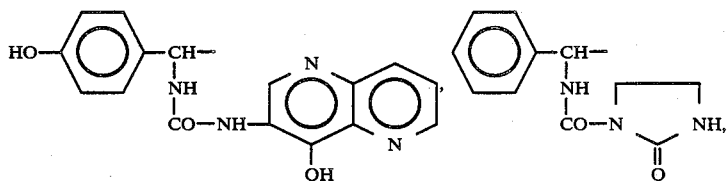

-continued
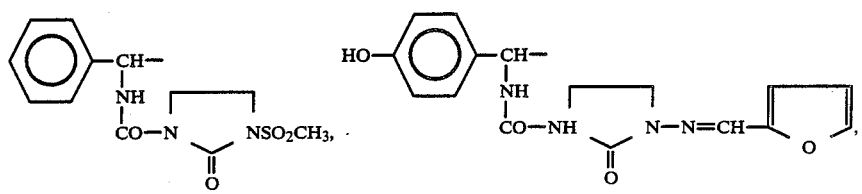
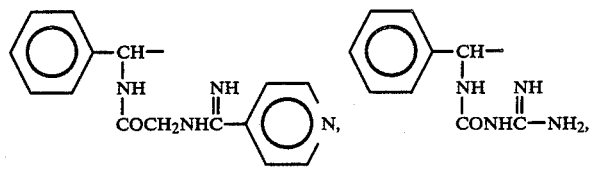
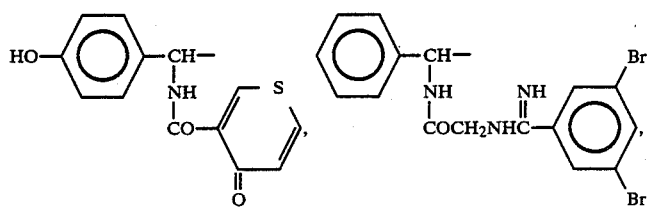
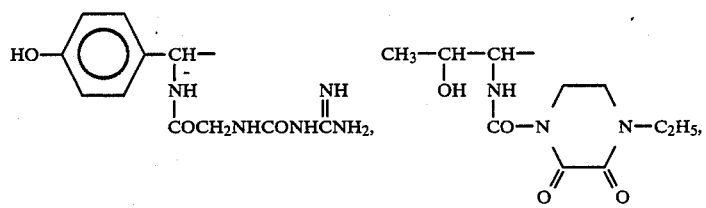
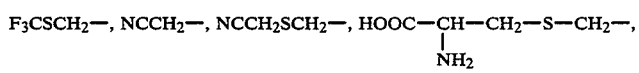
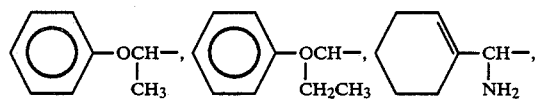
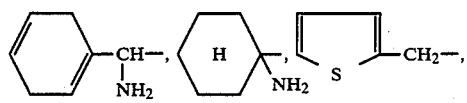
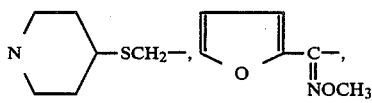
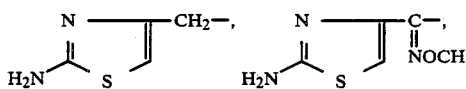
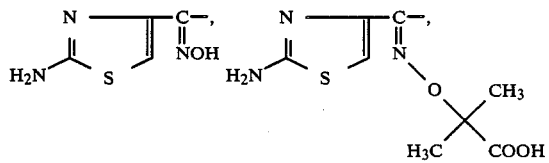

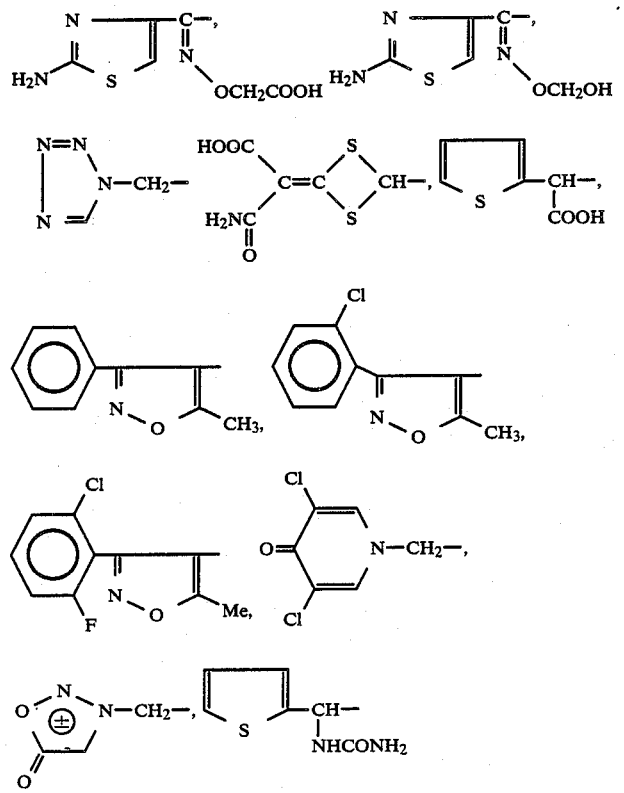

In case of that the above radicals have an imino ether bond, those having syn arrangement are preferable.

As the mono-valent substituent for $R_1$ in Q at 3-position of the cephalosporin derivatives according to the invention, following may be listed. Halogen atoms such as F, Cl, Br and the like; alkyl group such as methyl, ethyl, propyl and the like; alkenyl group such as vinyl, allyl and the like; alkinyl group; aromatic group such as phenyl, pyridyl and the like; trifluoromethyl radical; cyano radical; cyanoalkyl group such as cyanomethyl, cyanoethyl and the like; halogenoalkyl group such as chloromethyl, chloroethyl and the like; hydroxy radical; hydroxyalkylgroup such as hydroxymethyl, hydroxyethyl and the like; alkoxy group such as methoxy, ethoxy and the like; alkoxyalkyl group such as methoxymethyl, methoxyethyl and the like; thiol group; alkylthio group such as methylthio, ethylthio and the like; sulfen group; sulfino group; alkylsulfinylalkyl group such as methylsulfinylmethyl, methylsulfinylethyl and the like; alkylsulfonylalkyl group such as methylsulfonylmethyl, methylsulfonylethyl and the like; sulfone group; sulfoalkyl group such as sulfomethyl, sulfoethyl and the like; carboxyl radical; carboxyalkyl group such as carboxymethyl, carboxyethyl and the like; alkoxycarbonyl group such as methoxycarbonyl, ethoxycarbonyl and the like; alkoxycarbonylalkyl group such as methoxycarbonylmethyl, methoxycarbonylethyl and the like; carbamoyl radical; alkylcarbamoyl group such as methylcarbamoyl, ethylcarbamoyl and the like; hydroxycarbamoyl radical; hydroxycarbamoylalkyl group such as hydroxycarbamoylmethyl, hydroxycarbamoylethyl and the like; carbamoylalkyl group such as carbamoylmethyl, carbamoylethyl and the like; dialkylcarbamoyl group such as dimethylcarbamoyl, diethylcarbamoyl and the like; dialkylcarbamoylalkyl group such as dimethylcarbamoylmethyl, dimethylcarbamoylethyl and the like; hydroxyalkylcarbamoyl group such as hydroxymethylcarbamoyl, hydroxyethylcarbamoyl and the like; hydroxyalkylcarbamoylalkyl group such as hydroxymethylcarbamoylmethyl, hydroxymethylcarbamoylethyl and the like; amino radical; alkylamino group such as methylamino, ethylamino and the like; dialkylamino group such as dimethylamino, diethylamino and the like; aminoalkyl group such as aminomethyl, aminoethyl and the like; alkylaminoalkyl group such as methylaminomethyl, methylamino-ethyl and the like; dialkylaminoalkyl group such as dimethylaminomethyl, dimethylaminoethyl and the like; hydroxyiminoalkyl group such as hydroxyiminomethyl, hydroxyiminoethyl and the like; alkoxyiminoalkyl group such as methoxyiminomethyl, methoxyiminoethyl and the like; and aminocarboxyalkyl group such as aminocarboxyethyl, aminocarboxypropyl and the like. These substituents may be bonded in 2, 3 or 4-position of the pyridine ring.

As the mono-valent substituent for $R_2$, $R_3$ and $R_4$ in Q, followings may be listed as typical ones. A straight-chainalkyl group such as methyl, ethyl, n-propyl, n-butyl, n-pentyl, n-hexyl, n-decyl and the like; side-chain alkyl group such as isopropyl, isobutyl, sec-butyl, tert-butyl, isopentyl and the like; cycloalkyl group such as cyclopropyl, cyclobutyl, cyclopentyl, cyclohexyl, cycloheptyl and the like; alkoxy group such as methoxy, ethoxy, 2-methoxyethoxy and the like; phenyl radical; substituted phenyl group such as p-chlorophenyl, p-bromophenyl, p-methylphenyl, p-methoxyphenyl and the like; alkylcarbonyloxy group such as acetoxy, propionyloxy and the like; and trialkylsilyloxy group such as trimethylsilyloxy, triethylsilyloxy and the like. The radical of

may be bonded in 2, 3 or 4-position of the pyridine ring.

Among the cephalosporin derivatives according to the invention, basic compounds, for instance those having amino substituted heterocyclic ring in 7-position side-chain or having amino substituted pyridinium-methyl radical in 3-position side-chain may form acid addition salts. As acids for forming the salts, inorganic acids such as hydrochloric acid, hydrobromic acid, sulfuric acid, phosphoric acid and the like; and organic acids such as methanesulfonic acid, benzenesulfonic acid, toluenesulfonic acid, fumaric acid, maleic acid and the like may be listed.

While, acidic compounds, for instance those having carboxyl radical or sulfonic acid residue in 7-position side-chain, or having carboxyl substituted pyridinium-methyl radical in 3-position side-chain may form base addition salts. As such salts, metallic salts such as alkali metal salts (sodium salt, potassium salt and the like), alkaline earth metal salts (calcium salt, magnesium salt and the like) and so on; ammonium salts and organic base salts such as trimethylammonium salts, triethylammonium salts, pyridinium salts, picolinium salts, dicyclohexylammonium salts and the like may be listed.

According to the process of the invention, the cephalosporin derivatives shown by Formula I and salts thereof can be manufactured by reacting a 7-acylamino-3-acetoxymethyl cephalosporin represented by the formula

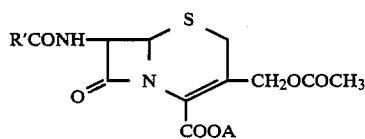

wherein R' is an organic residue known on β-lactam antibiotics, which residue may be protected, and A is a carboxyl protecting radical,
with a halogenated trialkylsilyl, reacting the resulting 7-acylamino-3-halomethyl cephalosporin represented by the formula

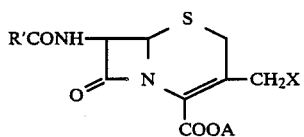

wherein R' and A have the meanings as referred to, and X is a halogen atom,
with a pyridine derivative represented by the formula

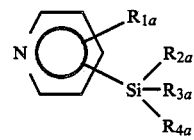

wherein $R_{1a}$ is hydrogen or a possibly protected mono-valent substituent, and $R_{2a}$, $R_{3a}$ and $R_{4a}$ are a possibly protected mono-valent substituent, respectively,
removing a possible protecting radical or radicals, and if necessary, converting the resulting compound into the salt.

As the protecting radical for the organic radical R' in 7-position, trityl, alkoxycarbonyl, allylalkoxycarbonyl and the like may be listed. As the carboxyl protecting radical A in 4-position, ester functional radicals which can easily be removed, for instance alkyl group and substituted alkyl group (t-butyl, 2,2,2-trihaloethyl and the like), benzyl and substituted benzyl group (p-methoxybenzyl, p-nitrobenzyl and the like), trialkylsilyl and the like may be listed. It is possible to make the both protecting radicals in 4 and 7-positions common, whereby an introduction and removal of same can be made easy. In this sense, it is quite preferable to employ trialkylsilyl group, for instance trimethylsilyl radical or the like as the common protecting radical.

In case of starting from 7-acylamino-3-acetoxymethyl-3-cephem-4-carboxylic acid to introduce trimethylsilyl radical, as the protecting one in each of 4 and 7-positions, this protecting operation can be done by suspending the starting carboxylic acid in a halogenated hydrocarbon solvent such as methylene chloride, chloroform, chloroethane and the like, or another inert organic solvent such as acetonitrile, propylnitrile or the like, adding a widely employed silylating agent such as mono or bis-trimethylsilylacetamide and more preferably N-methyl-N-trimethylsilyltrifluoroacetamide, and stirring the suspension at room temperature.

As the halogenated trialkylsilyl for converting the compound II into the compound III, trimethylsilyl iodide may be employed. This agent is used in amount of at least 1 equivalent and more preferably of 2 to 3 equivalents. This halogenating reaction also proceeds by stirring the reactants at room temperature.

It is not always necessary to isolate the resulting compound III of 3-halomethyl derivative. Therefore, it is sufficient only by concentrating the reaction mixture, removing the volatile substance, for instance the solvent, dissolving a residue in an inert solvent such as acetonitrile, and then adding tetrahydrofuran to decompose possible unreacted halogenating agent. The resulting solution containing the 3-halomethyl derivative is mixed with a solution containing the pyridine derivative (compound IV), which solution is prepared by dissolving the derivative in a suitable solvent such as acetonitrile (if the derivative has carboxyl, amino or the like radical in its pyridine skelton, it is preferable to protect the radical through a preliminary treatment using a silylating agent such as bis-trimethylsilyltrifluoroacetamide and the like). The reaction between the 3-halomethyl derivative (compound III) and pyridine derivative (compound IV) occurrs easily and proceeds only by stirring the mixture at room temperature. After completion of the reaction, water is added to the reaction mixture, which causes a removal of the protecting radical and precipitation of the desired compound which is to be obtained through a filtration. In general, the resulting compound is a crude one and thus refined. The refining may be carried out by a column chromatography.

According to a modified process of the invention, which is somewhat different from the operation as above, the cephalosporin derivatives shown by Formula I and salts thereof can be manufactured by reacting a compound represented by the formula

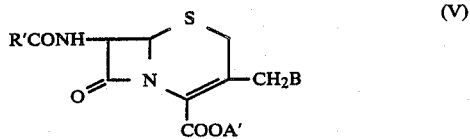

wherein R' has the meaning as referred to, A' is hydrogen or a carboxyl protecting radical, and B is a radical which can be substituted with a nucleophile,
with a pyridine derivative represented by the formula

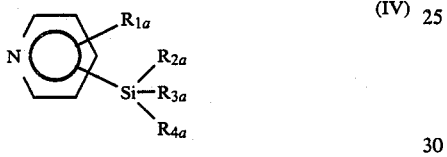

wherein $R_{1a}$, $R_{2a}$, $R_{3a}$ and $R_{4a}$ have the meanings as referred to,
removing a possible protecting radical or radicals, and if necessary, converting the resulting compound into the salt.

As the substituent B in 3-position of the starting material (compound V), acetoxy, propionyloxy, chloroacetoxy, acetylacetoxy and the like acyloxy group, halogen atom, carbamoyloxy and the like may be listed, but acetoxy is most preferable. While, as the carboxyl protecting radical A in 4-position, metal atoms such as sodium, potassium and the like; and easily removable ester functional radicals such as alkyl group, substituted alkyl group, benzyl, substituted benzyl and the like may be listed.

The reaction between the compounds IV and V can be carried out in a solvent and more particularly in water or a mixture of water and an organic solvent which easily mix with water, for instance acetone, dioxane, acetonitrile, dimethylformamide, dimethylsulfoxide, ethanol or the like. In general, the temperature of 10° to 100° C. is preferable for the reaction, but 20° to 80° C. is more preferable.

The pyridine derivative shown by Formula IV may be used in an amount of 1 to 10 equivalents and more preferably 3 to 5 equivalents and in order to accerate the reaction, a neutral salt such as potassium iodide, sodium iodide, potassium thiocyanate, sodium thiocyanate or the like may be added. In this case, it is preferable to carry out the reaction near neutral point and more preferably at pH range of 5 to 8 and therefor, sodium hydrogen carbonate may be added.

One of the starting materials, namely 7-acylaminocephalosporanic acid shown by Formaula II or V is available from the market and otherwise, it may be synthesized in a manner known per se. For instance, 3-[(acetyloxy)methyl]-7-[[(2-amino-4-thiazolyl)(methoxyimino)acetyl]amino]-8-oxo-5-thia-1-azabicyclo[4,2,0]oct-2-ene-2-carboxylic acid can be prepared, in accordance with the manner as disclosed in U.S. Pat. No. 4,152,432. The pyridine derivative shown by Formula IV as the other starting material may also be synthesized in a manner known per se. For instance, 3-trimethylsilylpyridine can be synthesized, in accordance with the manner as disclosed by F. Effenberger "Justus Liebigs Ann. Chem.", Page 842 (1979).

The cephalosporin derivatives and salts thereof according to the invention show a relatively wide antibacterial spectrum, inhibit the growth of various bacterias inclusive of etiological Gram-positive and negative pathogens, and show a relatively high antibacterial power. The $LD_{50}$ of the compounds is higher than 1 g/kg on the mouse and thus its toxicity is quite low to ensure the safety in use.

The process according to the invention for preparing such compounds shows advantages of that the reaction between the raw materials of 7-acylaminocephalosporanic acid and the pyridine derivative can be carried out under the mild condition of mere stirring at room temperature, to make operation and other treatments easy.

DOSING FORM AND AMOUNT

In case of preparing an infectious curing agent, effective component of which is one of the cephalosporin derivatives and salts according to the invention, there is no limitation in its medicine form and thus it may be made into one for oral or non-oral route, namely capsules, tablets, suger-coated tablets, ointments, suppositories and the like solid or semi-solid form, or solution, suspension, emulsion or the like liquid form. If necessary, conventional addives such as an auxiliary, stabilizer, wetting agent, emulsifier, buffer and the like may be composed.

A dosing amount of the compound for human depends on kind of the compound to be selected, condition of illness, age of a patient, form of the medicine and other variable factors but in case for an adult, 100 to 2000 mg/day is preferable.

DETAILED DESCRIPTION OF PREFERRED EMBODIMENTS

The invention will now be further explained with reference to Examples for preparing the compounds, Examples for testing pharmacological effects of the compounds and Examples for preparing pharmacological agents.

EXAMPLE 1

[6R-[6α,7β(Z)]]-1-[7-[[(2-Amino-4-thiazolyl)(methoxyimino)acetyl]amino]-2-carboxy-8-oxo-5-thia-1-azabicyclo[4,2,0]oct-2-en-3-yl]methyl-3-trimethylsilylpyridinium hydroxide, inner salt To a suspension of [6R-[6α,7β(Z)]]-1-[7-[[(2-Amino-4-thiazolyl)(methoxyimino)acetyl]amino]-2-carboxy-8-oxo-5-thia-1-azabicyclo[4,2,0]oct-2-ene-2-carboxylic acid (2.73 g) in $CH_2Cl_2$ (12 ml), N-methyl-N-trimethylsilyltrifluoroacetamide (3.74 ml) was added. After having stirred the mixture for 1.5 hr at room temperature, trimethylsilyl iodide (2.30 ml) was added to the reaction mixture, the stirring was continued for 0.5 hr at room temperature and then the reaction mixture was concentrated under reduced pressure. After having dissolved the residue in $CH_3CN$ (12 ml), THF (0.492 ml) was added and the mixture was stirred for 10 min to give a crude iodomethyl derivative as its CH$_3$CN solution.

A half amount (volume) of the solution of iodomethyl derivative was added to a stirred solution of 3-trimethylsilylpyridine (545 mg) in CH$_3$CN (2.5 ml) to stir the mixture for 3 hr at room temperature and then H$_2$O (0.290 ml) was added. The resulting precipitate was collected and washed with CH$_3$CN followed by Et$_2$O to give a yellowish brown powder (1.56 g).

After having dissolved the powder (500 mg) in H$_2$O (50 ml), a trace amount of insoluble material was filtered off and the remaining aqueous solution was lyophilized. The powdery residue was purified by preparative thin layer chromatography (silica gel, acetone-H$_2$O=4:1) followed by lyophilization to give the desired product (237 mg), as a pale yellow powder.

FAB-MS (m/z): 547 (M+H)$^+$.

| $^1$H—NMR (D$_2$O) | δ ppm: |
|---|---|
| 0.40 | (9H, s, SiMe$_3$), |
| 3.40 | (2H, ABq, J = 18.0Hz, Δν = 32.0Hz, C$_4$—H), |
| 3.93 | (3H, s, OMe), |
| 5.24 | (1H, d, J = 5.0Hz, C$_6$—H), |
| 5.78 | (1H, d, J = 5.0Hz, C$_7$—H), |
| 5.1–5.8 | (2H, m, —CH$_2$—N$^\oplus$), |
| 6.87 | (1H, s, thiazolyl-H), |
| 7.8–8.2 | 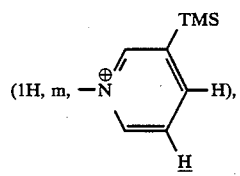 (1H, m), |
| 8.4–9.0 | 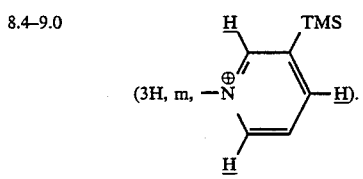 (3H, m). |

IR ($\nu_{max}^{KBr}$) cm$^{-1}$: 3400, 1770, 1610, 1530, 1035.

EXAMPLE 2

[6R-[6α,7β(Z)]]-1-[7-[[(2-Amino-4-thiazolyl)(methoxyimino)acetyl]amino]-2-carboxy-8-oxo-5-thia-1-azabicyclo[4,2,0]oct-2-en-3-yl]methyl-4-trimethylsilylpyridinium hydroxide, inner salt A solution of iodomethyl derivative (½ volume, prepared by similar reaction as described in Example 1) was added to a stirred solution of 4-trimethylsilylpyridine (545 mg) in CH$_3$CN (2.5 ml). The mixture was stirred for 3 hr at room temperature and then H$_2$O (0.290 ml) was added. The resulting precipitate was collected and washed with CH$_3$CN followed by Et$_2$O to give a yellowish brown powder (1.26 g).

After having dissolved the powder (500 mg) in H$_2$O (50 ml), similar operations as described in Example 1 were carried out to give the desired product (190 mg), as a pale yellow powder.

FAB-MS (m/z): 547 (M+H)$^+$.

| $^1$H—NMR (D$_2$O) | δ ppm: |
|---|---|
| 0.38 | (9H, s, SiMe$_3$), |
| 3.38 | (2H, ABq, J = 18.0Hz, Δν = 32.0Hz, C$_4$—H), |
| 3.94 | (3H, s, OMe), |
| 5.25 | (1H, d, J = 5.0Hz, C$_6$—H), |
| 5.77 | (1H, d, J = 5.0Hz, C$_7$—H), |
| 5.1–5.8 | (2H, m, —CH$_2$—N$^\oplus$), |
| 6.91 | (1H, s, thiazolyl-H), |
| 8.15 | 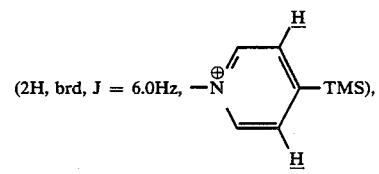 (2H, brd, J = 6.0Hz), |
| 8.75 | 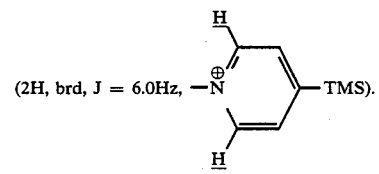 (2H, brd, J = 6.0Hz). |

IR ($\nu_{max}^{KBr}$) cm$^{-1}$: 3400, 1770, 1610, 1530, 1035.

EXAMPLE 3

[6R-[6α,7β(Z)]]-1-[7-[[(2-Amino-4-thiazolyl)(methoxyimino)acetyl]amino]-2-carboxy-8-oxo-5-thia-1-azabicyclo[4,2,0]oct-2-en-3-yl]methyl-4-methoxy-3-trimethylsilylpyridinium hydroxide, inner salt A solution of iodomethyl derivative (½ volume, prepared by similar reaction as described in Example 1) was added to a stirred solution of 4-methoxy-3-trimethylsilylpyridine (653 mg) in CH$_3$CN (2.5 ml). The mixture was stirred for 3 hr at room temperature and then H$_2$O (0.290 ml) was added. The resulting precipitate was collected and washed with CH$_3$CN followed by Et$_2$O to give a yellowish brown powder (1.73 g).

After having dissolved the powder (500 mg) in H$_2$O (50 ml), similar operations as described in Example 1 were carried out to give the desired product (240 mg), as a pale yellow powder.

FAB-MS (m/z): 577 (M+H)$^+$.

| $^1$H—NMR (D$_2$O) | δ ppm: |
|---|---|
| 0.33 | (9H, s, SiMe$_3$), |
| 3.38 | (2H, ABq, J = 18.0Hz, Δν = 32.0Hz, C$_4$—H), |
| 3.95 | (3H, s, N—OMe), |
| 4.08 | (3H, s, C—OMe), |
| 5.0–5.4 | (3H, m, C$_6$—H, and —CH$_2$—N$^\oplus$), |
| 5.76 | (1H, d, J = 5.0Hz, C$_7$—H), |
| 6.87 | (1H, s, thiazolyl-H), |
| 7.34 | 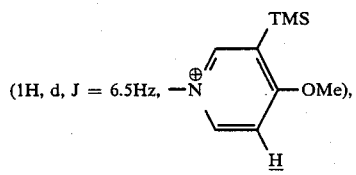 (1H, d, J = 6.5Hz), |

-continued

| ¹H—NMR (D₂O) | δ ppm: |
|---|---|
| 8.1-8.8 | (2H, m, —N⊕ pyridinium with H, TMS, OMe, H) |

IR ($\nu_{max}^{KBr}$) cm⁻¹: 3400, 1760, 1620, 1530, 1035.

EXAMPLE 4

[6R-[6α,7β(Z)]]-1-[7-[[(2-Amino-4-thiazolyl)(methoxyimino)acetyl]amino]-2-carboxy-8-oxo-5-thia-1-azabicyclo[4,2,0]oct-2-en-3-yl]methyl-4-(4,5-dihydro-4,4-dimethyl-2-oxazolyl)-3-trimethylsilylpyridinium hydroxide, inner salt A solution of iodomethyl derivative (⅓ volume, prepared by similar reaction as described in Example 1) was added to a stirred solution of 4-(4,5-dihydro-4,4-dimethyl-2-oxazolyl)-3-trimethylsilylpyridine (596 mg) in CH₃CN (2.5 ml). The mixture was stirred for 3 hr at room temperature and then H₂O (0.196 ml) was added. The resulting precipitate was collected and washed with CH₃CN followed by Et₂O to give a yellowish brown powder (1.27 g).

After having dissolved the powder (500 mg) in H₂O (50 ml), similar operations as desribed in Example 1 were carried out to give the desired product (198 mg), as a pale yellow powder.

FAB-MS (m/z): 644 (M+H)⁺.

| ¹H—NMR (D₂O) | δ ppm: |
|---|---|
| 0.40 | (9H, s, SiMe₃), |
| 1.42 | (6H, s, oxazoline with Me, Me), |
| 3.42 | (2H, ABq, J = 18.0Hz, Δν = 32.0Hz, C₄—H), |
| 3.91 | (3H, s, OMe), |
| 4.33 | (2H, s, O—CH₂—) |
| 5.21 | (1H, d, J = 5.0Hz, C₆—H), |
| 5.73 | (1H, d, J = 5.0Hz, C₇—H), |
| 5.1-5.7 | (2H, m, —CH₂—N⊕), |
| 6.80 | (1H, s, thiazolyl-H), |
| 8.13 | (1H, brd, J = 6.0Hz, pyridinium with TMS, O, N) |
| 8.8-9.0 | (2H, m, pyridinium with H, TMS, O, N, H) |

IR ($\nu_{max}^{KBr}$) cm⁻¹: 3400, 1780, 1615, 1535.

EXAMPLE 5

[6R-[6α,7β(Z)]]-1-[7-[[(2-Amino-4-thiazolyl)(methoxyimino)acetyl]amino]-2-carboxy-8-oxo-5-thia-1-azabicyclo[4,2,0]oct-2-en-3-yl]methyl-4-carboxy-3-trimethylsilylpyridinium hydroxide, inner salt N,O-Bis(trimethylsilyl)trifluoroacetamide (1.28 ml) was added to a suspension of 3-trimethylsilyl-4-pyridinecarboxylic acid (937 mg) in CH₃CN (8.0 ml). The mixture was stirred for 0.5 hr at room temperature. To the reaction mixture, a solution of iodomethyl derivative (⅔ volume, prepared by similar reaction as described in Example 1) was added. The mixture was stirred for 3 hr at room temperature and then H₂O (0.600 ml) was added. The resulting precipitate was collected and washed with CH₃CN followed by Et₂O to give a yellowish brown powder (1.73 g).

After having dissolved the powder (500 mg) in H₂O (50 ml), similar operations as desribed in Example 1 were carried out to give the desired product (320 mg), as a pale yellow powder.

FAB-MS (m/z): 591 (M+H)⁺.

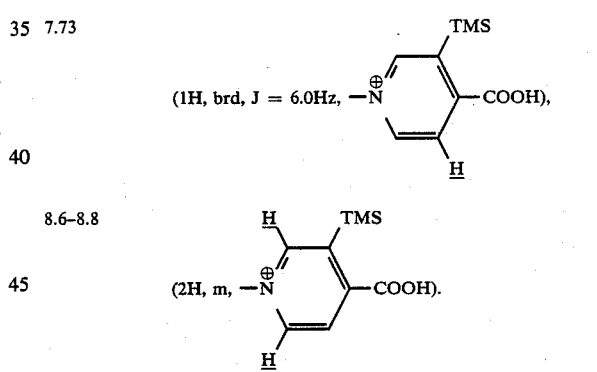

| ¹H—NMR (D₂O) | δ ppm: |
|---|---|
| 0.38 | (9H, s, SiMe₃) |
| 3.39 | (2H, ABq, J = 18.0Hz, Δν = 32.0Hz, C₄—H), |
| 3.91 | (3H, s, OMe), |
| 5.18 | (1H, d, J = 5.0Hz, C₆—H), |
| 5.73 | (1H, d, J = 5.0Hz, C₇—H), |
| 5.2-5.8 | (2H, m, —CH₂—N⊕), |
| 6.88 | (1H, s, thiazolyl-H), |
| 7.73 | (1H, brd, J = 6.0Hz, —N⊕ pyridinium with TMS, COOH, H), |
| 8.6-8.8 | (2H, m, —N⊕ pyridinium with H, TMS, COOH, H). |

IR ($\nu_{max}^{KBr}$) cm⁻¹: 3400, 1770, 1615, 1535, 1380.

PHARMACEUTICAL TEST EXAMPLE 1

(Antibacterial spectrum and antibacterial power)

Each series of dilution was prepared with use of testing compounds prepared by the Examples and control compound of Gentamicin as well as a liquid medium. The minimum inhibitory concentration (MIC in μg/ml) to each pathogen (seeding amount: 10⁶ cells/ml) was determined, in accordance with the standard method (agar plate dilution method) by the Chemotherapy Society of Japan. Results are shown in following Table.

The control compound of Gentamicin has been known as one of water soluble basic antibiotics having a wider antibacterial spectrum and showing a higher antibacterial power but the results given in the Table apparently show a fact that the compounds according to the invention are superior than the Gentamicin in both of the antibacterial spectrum and antibacterial power.

| Strains | Examples 1 | 2 | 3 | Gentamicin |
|---|---|---|---|---|
| E. coli NIH | <0.20 | <0.20 | 0.78 | 0.78 |
| E. coli K-12 | 0.39 | 0.78 | 0.78 | 0.78 |
| C. fleundii NIH 10018-68 | <0.20 | <0.20 | 0.78 | 0.39 |
| K. pneumoniae NCTC 9632 | 0.39 | 0.78 | 0.78 | 0.78 |
| S. typhi T-287 | <0.20 | 0.39 | 0.39 | 0.78 |
| S. flexneri 2a EW-10 | <0.20 | 0.39 | 0.39 | 3.13 |
| P. vulgaris OX-19 | <0.20 | <0.20 | <0.20 | 3.13 |
| P. rettgeri NIH 96 | <0.20 | <0.20 | <0.20 | <0.20 |
| P. aeruginosa Nc-5 | 1.56 | 6.25 | 6.25 | 3.13 |

PHARMACEUTICAL TEST EXAMPLE 2

(Acute toxicity)

Some compounds according to the invention were tested to evaluate their acute toxicity in mouse.

ICR mice of male sex (body weight of 29 to 32 g) and female sex (body weight of 21 to 26 g), each mouse having age of 6 weeks were selected for the experiment. Each of the testing compounds (Example 1 to 3) was dissolved in physiological salt solution and the resulting solution was dosed to the mice in oral or abdominal route.

A weighing and observation on general behavior were carried out just before the dosage and each day after the same. Each of died mice was subjected without delay to an autopsy to check same. All of living mice were killed at 14th day from the dosage to carry out the autopsy.

An $LD_{50}$ was calculated in accordance with the Leed and Munch's method to find that the value of each compound is more than 1 g/kg.

PRESCRIPTIONAL EXAMPLE 1 (INJECTION)

The compound (0.5 g) prepared by the Example 1 was dissolved 0.9% NaCl solution to make total volume of the resulting solution to 10 ml. The solution was charged in a vial to seal the same.

PRESCRIPTIONAL EXAMPLE 2 (DRY POWDER FOR INJECTION)

The compound (0.5 g) prepared by the Example 2 was aseptically charged and sealed in a glass vial.

The dry powder accommodated in the vial can be dissolved in distilled water for injection to make total volume of 10 ml and then immediately injected to a patient.

PRESCRIPTIONAL EXAMPLE 3 (TABLET)

Following ingredients were composed and treated in a conventional manner to prepare tablets.

| Product of Example 3 | 150 (mg) |
|---|---|
| Lactose | 20 |
| Corn starch | 5 |
| Hydroxypropylcellulose | 4 |
| Magnesium stearate | 1 |
| | 180 mg/tablet |

PRESCRIPTIONAL EXAMPLE 4 (GRANULE)

Following ingredients were composed and treated in a conventional manner to prepare granules.

| Product of Example 1 | 150 (mg) |
|---|---|
| Lactose | 20 |
| Corn starch | 5 |
| Hydropropylcellulose | 5 |
| | 180 mg/package |

PRESCRIPTIONAL EXAMPLE 5 (OINTMENT)

Following ingredients were composed and treated in a conventional manner to prepare an ointment.

| Product of Example 1 | 0.5 (g) |
|---|---|
| Vaselline | 100 |
| | 100.5 g |

PRESCRIPTIONAL EXAMPLE 6 (SUPPOSITORY)

Following ingredients were composed and treated in a conventional manner to prepare suppositories.

| Product of Example 3 | 0.2 (g) |
|---|---|
| Witep-Sol H-12 | 1.6 |
| Maleic acid | 0.2 |
| | 2.0 g/piece |

We claim:
1. A cephalosporin antibiotic of the formula

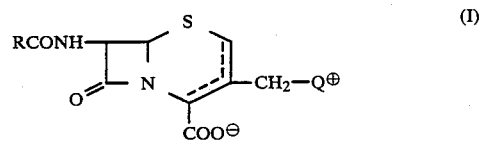

wherein the dotted lines mean a possible double bond; R is selected from the group consisting of

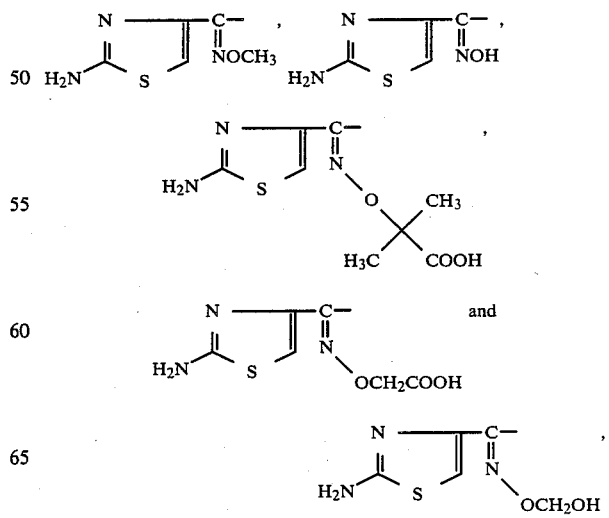

Q is

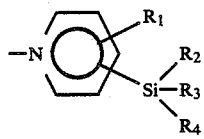

in which $R_1$ is hydrogen, an alkyl group having 1 to 3 carbon atoms, an alkoxy group having 1 to 3 carbon atoms, or an oxazolyl group substituted with 1 or 2 alkyl groups having 1 to 3 carbon atoms, and $R_2$, $R_3$ and $R_4$ are each an alkyl group having 1 to 3 carbon atoms;
and a non-toxic salt thereof.

2. A pharmaceutical composition for use in human or veterinary medicine comprising an antibacterially effective amount of at least one cephalosporin antibiotic of claim 1 in association with a pharmaceutical carrier or excipient.

3. A method of combatting a bacterial infection in a human or a warm blooded animal comprising administering an antibacterially effective amount of at least one cephalosporin antibiotic of claim 1.

4. The cephalosporin antibiotic as set forth in claim 1 which is [6R-[6α,7β(Z)]]-1-[7-[[(2-amino-4-thiazolyl)-(methoxyimino)acetyl]amino]-2-carboxy-8-oxo-5-thia-1-azabicyclo[4,2,0]oct-2-en-3-yl]methyl-3-trimethyl-silylpyridinium hydroxide, inner salt, and a salt thereof.

5. The cephalosporin antibiotic as set forth in claim 1 which is [6R-[6α,7β(Z)]]-1-[7-[[(2-amino-4-thiazolyl)-(methoxyimino)acetyl]amino]-2-carboxy-8-oxo-5-thia-1-azabicyclo[4,2,0]oct-2-en-3-yl]methyl-4-trimethyl-silylpyridinium hydroxide, inner salt, and a salt thereof.

6. The cephalosporin antibiotic as set forth in claim 1 which is [6R-[6α,7β(Z)]]-1-[7-[[(2-amino-4-thiazolyl)-(methoxyimino)acetyl]amino]-2-carboxy-8-oxo-5-thia-1-azabicyclo[4,2,0]oct-2-en-3-yl]methyl-4-methoxy-3-trimethylsilylpyridinium hydroxide, inner salt, and a salt thereof.

7. The cephalosporin antibiotic as set forth in claim 1 which is [6R-[6α,7β(Z)]]-1-[7-[[(2-amino-4-thiazolyl)(methoxyimino)acetyl]amino]-2-carboxy-8-oxo-5-thia-1-azabicyclo[4,2,0]oct-2-en-3-yl]methyl-4-(4,5-dihydro-4,4-dimethyl-2-oxazolyl)-3-trimethylsilylpyridinium hydroxide, inner salt, and a salt thereof.

8. The cephalosporin antibiotic as set forth in claim 1 which is [6R-[6α,7β(Z)]]-1-[7-[[(2-amino-4-thiazolyl)-(methoxyimino)acetyl]amino]-2-carboxy-8-oxo-5-thia-1-azabicyclo[4,2,0]oct-2-en-3-yl]methyl-4-carboxy-3-trimethylsilylpyridinium hydroxide, inner salt, and a salt thereof.

* * * * *